United States Patent [19]

von Bonin

[11] Patent Number: 5,374,448
[45] Date of Patent: Dec. 20, 1994

[54] PROCESS FOR THE PRODUCTION OF STIFFENING MATERIALS CONTAINING HYDRAULIC BINDERS, IN PARTICULAR OF PLASTER BANDAGES

[75] Inventor: Wulf von Bonin, Odenthal, Germany

[73] Assignee: Bayer Aktiengesellschaft, Leverkusen, Germany

[21] Appl. No.: 902,195

[22] Filed: Jun. 22, 1992

[30] Foreign Application Priority Data

Jun. 29, 1991 [DE] Germany .................... 4121626

[51] Int. Cl.$^5$ .................... A61F 13/04; B05D 1/40
[52] U.S. Cl. .................... 427/2.31; 427/177; 427/194; 427/365; 427/369; 427/403
[58] Field of Search .................... 427/2, 177, 286, 211, 427/365, 194, 210, 369, 403, 412; 602/8, 900

[56] References Cited

U.S. PATENT DOCUMENTS

| | | | |
|---|---|---|---|
| 1,524,573 | 1/1925 | Respess | 427/211 |
| 2,655,148 | 10/1953 | Eberi et al. | 602/8 |
| 2,914,421 | 11/1959 | Wiener | 427/2 |
| 2,940,868 | 6/1960 | Patchell | 427/2 |
| 2,948,634 | 8/1960 | Furendal et al. | 427/2 |
| 2,954,766 | 10/1960 | Foglia | 427/2 |
| 3,649,319 | 3/1972 | Smith | 106/111 |
| 3,682,738 | 8/1972 | Smith | 427/198 |
| 3,745,998 | 7/1973 | Rose | 128/DIG. 15 |
| 3,941,632 | 3/1976 | Swedenberg et al. | 427/403 |
| 4,076,019 | 2/1978 | Sain | 427/2 |
| 4,117,183 | 9/1978 | Long | 427/286 |
| 4,117,197 | 9/1978 | Krejci et al. | 427/369 |
| 4,153,753 | 5/1979 | Woodman et al. | 427/369 |
| 4,286,586 | 9/1981 | Potts | 427/2 |
| 4,335,158 | 6/1982 | Beede et al. | 427/2 |
| 4,376,438 | 3/1983 | Straube et al. | 427/2 |
| 4,544,683 | 10/1985 | Müller et al. | 427/2 |
| 4,672,956 | 6/1987 | Potter et al. | 427/2 |
| 4,741,918 | 5/1988 | Nagy de Nagybaezon et al. | 427/194 |
| 4,792,466 | 12/1988 | McWilliams et al. | 427/177 |
| 4,898,159 | 2/1990 | Buese et al. | 427/2 |
| 5,124,177 | 6/1992 | Kasmark, Jr. et al. | 118/63 |
| 5,308,642 | 5/1994 | von Bonin et al. | 602/8 |

FOREIGN PATENT DOCUMENTS

| | | |
|---|---|---|
| 1767434 | 5/1968 | Germany . |
| 3001854 | 1/1980 | Germany . |
| 3706094 | 2/1987 | Germany . |
| 4019310 | 6/1990 | Germany . |
| 4036200 | 11/1990 | Germany . |
| 1504972 | 3/1978 | United Kingdom . |
| 2106012 | 4/1983 | United Kingdom ............. 427/194 |

*Primary Examiner*—Shrive Beck
*Assistant Examiner*—Diana Dudash
*Attorney, Agent, or Firm*—Sprung Horn Kramer & Woods

[57] ABSTRACT

Improved stiffening materials containing hydraulic binders are obtained by applying a hydraulic binder, if appropriate in mixture with reactive binders, in powder form to a sheetlike material, for example a bandage fabric, compacting the hydraulic binder in contact with the sheetlike material, and winding the sheetlike material thus provided with the compacted hydraulic binder into rolls.

14 Claims, No Drawings

PROCESS FOR THE PRODUCTION OF STIFFENING MATERIALS CONTAINING HYDRAULIC BINDERS, IN PARTICULAR OF PLASTER BANDAGES

Plaster bandages have previously usually been produced by making plaster of Paris into a paste using a binder dissolved in methylene chloride, for example a binder based on modified cellulose, and applying this paste to the bandage material, for example a cotton fabric, by means of a knife. The methylene chloride is then removed by evaporation, as a result of which the binder binds the plaster to the bandage material. The plaster-containing bandage material can now be cut and rolled without the plaster peeling off. The plaster-containing bandage material cut into strips is then wound relatively loosely onto perforated, tubular cores. The plaster bandage thus formed is activated by dipping it into water. As a result, the hydrophilically bound plaster forms a plaster paste which solidifies after application and produces a plaster cast.

This production process for plaster bandages has the disadvantage that solvents have to be used, for example methylene chloride, which in today's view are only tolerable, if at all, in small amounts and whose removal from the waste air is also very complicated and expensive. A similar procedure is used for the production of stiffening materials suitable for practical application.

According to an earlier patent application by Applicants, not published before the filing date of the present application, stiffening materials containing hydraulic binders are produced by mixing a hydraulic binder in powder form with a reactive binder, applying this mixture to a sheetlike material, winding the sheetlike material thus coated into rolls and allowing the setting reaction of the reactive binder to proceed before, during and/or after winding.

It has now been found that improved stiffening materials containing hydraulic binders are obtained by
applying a hydraulic binder, if appropriate in mixture with other binders, in powder form to a sheet-like material,
compacting the hydraulic binder, if appropriate in the form of stripes or patterns, in contact with the sheetlike material, and
winding the sheetlike material thus provided with compacted hydraulic binder into rolls.

The essential feature of the present invention is compaction of the hydraulic binder in contact with the sheetlike material. The use of additional, preferably reactive but also non-reactive binders is advantageous. Preferably, compaction according to the invention is carried out in such a way that the hydraulic binder loses its pulverulent and free-flowing character in the process. For example, the procedure can be such that a sheetlike material charged with hydraulic binder in an amount of 200 to 800 g/m$^2$ is guided through a roll nip having a width of 0.02 to 0.3 mm, preferably 0.05 to 0.1 mm. Compaction is considered especially effective if the hydraulic binder thereafter looks homogeneous-compact or has an opaque transparent appearance.

It is also possible to carry out compaction, for example, by means of stamps or presses.

An advantageous embodiment of the present invention is characterised in that compaction of the hydraulic binder is carried out on one or between two or more layers of sheetlike material. The latter leads to a sandwich-like structure of the stiffening material, for example the plaster bandage. A sandwich structure can also be achieved by the structural sequence of compacted hydraulic binder/sheetlike support material/compacted hydraulic binder.

If desired, the surface of the compacted binder layer can be provided with embossed patterns, for example in order to increase the surface area, for decorative reasons or for labelling purposes.

In a further advantageous embodiment of the present invention, the hydraulic binder is present in the form of individual horizontal stripes on one side or both sides of the sheetlike material, leading to a rope-ladder structure.

A sandwich-like structure gives the stiffening material before setting of the hydraulic binder particularly good processing properties. The hydraulic binder has virtually no longer any tendency to trickle off during winding into a roll or in the presence of other mechanical influences even if it contains little or no reactive binder. Nevertheless, the additional use of reactive binders is preferred since in this case there is little to no tendency to smear and drip off when impregnated with water for setting the hydraulic binder.

Accordingly, apart from the embodiment of the single-layer sheetlike material, a particularly favourable embodiment of the present invention is characterised in that for the production of plaster bandages usable in medicine
a plaster-based hydraulic binder is mixed with a reactive binder,
this mixture is applied to a sheetlike material,
the coating thus obtained is covered with a further sheetlike material (this step is omitted if plaster bandages having only a single layer of sheetlike material are produced),
the binder mixture is compacted until it loses its free-flowability,
the product thus provided with a compacted binder layer is wound loosely into rolls and
the setting reaction of the reactive binder is allowed to proceed before, during and/or after winding.

Suitable hydraulic binders are in particular the gypsum grades customary for the production of medical plaster bandages. They are preferably partially hydrated gypsums, for example so-called $\alpha$ - and/or $\beta$-stuccoe-gypsum whose setting time can be less than 10 minutes.

However, other hydraulic binders by themselves or in a mixture are also suitable, in particular also for the production of stiffening materials for practical application. Examples are: other gypsum modifications, such as stucco, such as $\alpha$-gypsum, $\beta$-gypsum and anhydrite, and Portland cement, high-alumina cements, aluminosilicate quick-setting cements, Sorell cements, zinc oxide cements, Puzzolan cements and other inorganic powders which harden on reaction with water having cement-like character. They can also be organic or mixed inorganic/organic powders or preparations which harden on reaction with water.

The hydraulic binders in pulverulent form to be used for the invention can also be mixtures of two or more components. If desired, customary accelerators, for example soluble sulphates, or retarding or rheological additives, for example proteins or cellulose derivatives, can have been added to the hydraulic binder.

If desired, the hydraulic binder can be used in a mixture with reactive binders. Suitable reactive binders are a wide range of reactive binders or binder mixtures known as such, which can be applied, preferably in liquid form, as one- or multi-component systems to the hydraulic binder and whose viscosity can then be increased, for example as a result of crosslinking or other increase in molecular weight, by reaction of the mixture components and/or by exposure to heat, air, humidity, light and/or by chemical reaction with a reactant which, if desired, is additionally introduced and/or with a catalyst, free-radical former or other initiator.

This increase in viscosity can take place, at least in part, on the hydraulic binder and/or in the subsequently formed roll or be brought to completion therein.

Examples of reactive binders are: silicates of the waterglass type applicable without the aid of organic solvents, plaster- or cement-binding salts, epoxides, polyepoxides, epoxy curing agent combinations, double bond systems polymerising upon exposure to air, ion or free-radical formers, for example mono-, di- or polyolefinic monomers, for example of the cyanoacrylate, acrylate, vinyl ester, allyl ester or allyl ether type, of the silane, siloxane or silicone type (see, also, German Offenlegungsschrift 2,357,931), of the alkyd resin and reactive alkyd resin thinner type, of the cyanate resin, phenolic resin, formaldehyde resin, methylol compound, methylol ether type, of the (poly)isocyanate type (for example bifunctional and higher functional polyisocyanates containing urethonimine, oxadiazintrione, iminocyanates containing urethonimine-, oxadiazintrione-, iminoisocyanurate-, uretdione-, isocyanurate-, uretdiimine-, biuret- and/or urea groups based preferably on aliphatic polyisocyan and the polyisocyanates and isocyanate prepolymers mentioned later in conjunction with polyol polyisocyanate combinations), which, for example, can be made to react with water or polyols, possibly with participation of the moisture contained in the roll, with the formation of polyurethanes, polyureas, polycarbodiimides and/or polyisocyanurates.

Polycarboxylic acids, alginates, aluminates, cellulose and starch compounds are also suitable, which, for example, may be subject to precipitation or hardening due to the calcium ions or aluminium ions from the hydraulic binder with which they are in contact.

Preferably used reactive binders are combinations of one or more polyols and one or more polyisocyanates. Combinations of polyols and polyisocyanates can, if desired, contain further components, preferably those retarding or accelerating the reaction between the polyol and the polyisocyanate. Accelerating additives are preferred. Those further components, for example catalysts, can be used, if desired, in amounts of 0.05 to 3% by weight (relative to the mixture of polyol and polyisocyanate).

Examples of suitable accelerating additives are amine or organometallic compounds or else other compounds known in polyurethane chemistry as catalytically active compounds. These can also be integrated in the polyol, for example in the form of amino groups.

The components of the reactive binder can be admixed to the pulverulent hydraulic binder in mixed form, separately and simultaneously or preferably in succession.

The reactive binder can be admixed to the hydraulic binder, preferably plaster, for example, in amounts of 0 to 50% by weight, preferably 0.5 to 10% by weight, in particular 2 to 6% by weight. It is advantageous to ensure that the mixture of hydraulic binder and reactive binder still maintains pulverulent, sprinklable character.

It is furthermore advantageous but not absolutely necessary to apply a freshly prepared mixture of hydraulic and reactive binder immediately or within a few hours after preparation to the sheetlike material. Before application to the sheetlike material, it is possible, if desired, to add further additives, such as wetting agents, surfactants, flow-improving agents, coloured pigments and/or biocides, to the mixture of hydraulic and reactive binder or an individual component thereof.

For example, 100 to 1000 g, preferably 150 to 800 g, in particular 200 to 600 g, of hydraulic binder or mixtures of hydraulic, reactive and/or non-reactive binders can be applied to 1 m$^2$ of the sheetlike material.

Suitable polyols used in the preferred reactive binders, i.e. the combinations of polyols and polyisocyanates, are preferably the linear and branched polyester polyols which are industrially used in polyurethane chemistry and are preferably liquid at room temperature and in particular polyether polyols. Of particular interest are trifunctional and higher functional types which can be obtained by adduct formation of ethylene oxide and/or propylene oxide with trifunctional and higher functional initiators, for example with trimethylolpropane, glycerol, pentaerythritol, sorbitol, sugar or sugar mixtures, ammonia, triethanolamine, ethylenediamine, polyethylenepolyamine, polypropylenepolyamine, ethanolamine and/or diethanolamine and have OH numbers of more than 5, preferably between 30 and 400, in particular between 150 and 300.

Suitable polyisocyantes are the aliphatic, araliphatic, heterocyclic and aromatic polyisocyanates industrially used in polyurethane chemistry. Preferably, those polyisocyanates are used whose vapour pressure in the range from 10° to 50° C. is very low. If this is the case, their handling does not involve any risk. Polyisocyanates of this type are preferably aliphatic polyisocyanates which are liquid at room temperature, such as polymerised, trimerised, biuretised, allophanatised hexamethylene diisocyanate, isophorone diisocyanate or hexamethylene diisocyanate, isophorone diisocyanate reacted with small amounts of water or carbon dioxide, or those aromatic or non-aromatic polynuclear polyisocyanate types such as are industrially accessible by phosgenation of aniline/formaldehyde condensation products and hydrogenated forms thereof. Other liquid polyisocyanates are also suitable, as are aliphatic-aromatic mixed types, for example those based on isophorone diisocyanate or toluylene diisocyanate or so-called isocyanate prepolymers, i.e. isocyanato-containing, preferably liquid oligomeric reaction products of polyols with polyisocyanates.

It is advantageous if the components of such reactive binder mixtures of polyol and polyisocyanate are soluble in one another, although this is not a requirement. Polyol mixtures and/or polyisocyanate mixtures can also be used.

The stoichiometric ratio of OH to NCO groups in the polyol/polyisocyanate mixtures can vary within wide limits. Stoichiometric ratios with variations of $+/-50\%$ by weight are preferably maintained. In specific cases, it is also possible to reduce the ratio of the polyisocyanates and polyols used to 3% by weight each of the stoichiometrically equivalent amount or to even less. The use of reactive binders containing 30 to 90% by weight of the stoichiometrically required amount of polyisocyanate components, relative to the polyol component, is particularly preferred.

These ratios apply even in those cases where the reactive combination of liquid binder components is prepared before, during or after introduction into the pulverulent hydraulic binder.

Instead of or in addition to reactive binders, it is also possible to use non-reactive binders, for example ethoxylated abietic acid.

Suitable sheetlike materials to which a hydraulic binder or mixture of hydraulic and/or reactive binders is applied, hereinafter simply called "bandage fabric", are a wide variety of flexible, preferably textile, substrates. They can be composed, for example, of filaments, fibres, wires or slit-film ribbons. Preferably they are non-wovens, papers, knitted fabrics or woven fabrics or mixed forms thereof.

Bandage fabrics manufactured from cotton, such as are customary for conventional manufacture of plaster bandages, are preferably used. However, suitable textile substrates are also those which have been produced using, for example, glass fibres, carbon fibres, polyaramid fibres, metal fibres, polyolefine fibres, polyolefine high-modulus fibres, polyamide high-modulus fibres and polyester high-modulus fibres, other polyester fibres, other polyacrylonitrile fibres, silk, other polyamide fibres and fibres from improved cellulose and from fibre mixtures and/or filament mixtures. So-called fine fibres, hollow fibres, and microfibres are also suitable.

The single-layer or multi-layer, preferably single- or two-layer (sandwich-like) sheetlike material can be cut to size in terms of length and width, for example to give individual bandages, before or after application of the hydraulic binder or preferably before or after winding which serves for finishing purposes.

Application of the pulverulent binder, which may contain completely reacted or not completely reacted reactive binder and/or non-reactive binder, can take place in the form of sheets or in the form of stripes or other patterns by the reverse or preferably the direct process, for example by sprinkling, blowing, knife application, electrostatically or by any other process not requiring any solvents.

The hydraulic binder or binder-mixture can form a homogeneous area on the sheetlike material, which, if desired, can later on be provided with patterns, for example with stripey patterns by means of an embossing process. However, the binder can also be applied on one or both sides in the form of stripes, points, interrupted areas or in the form of patterns which may have different thicknesses, for example in order to allow better penetration of the impregnating water or to achieve selective stiffening effects. Preferably, the binder is applied in the form of stripes which are parallel to the winding axes or in the form of points or patterns.

If desired, a layer of the binder once applied can be made to form inhomogeneous distributions and/or more permeable regions, for example by shaking, vibrating or pneumatic processes.

The production of plaster bandages having a two-sided ladder structure can be easily effected in various ways. For example, depending on the type of ladder structure desired, a ribbed runner thread (for example of the rope ladder or "tank-track" type) made of metal or plastic can be sprinkled with binder, a layer of bandage fabric can then be placed on top, this layer can then again be sprinkled with binder and the runner thread together with the layer of be sprinkled bandage fabric can be run through a pair of rolls. During this, the ladder structure of the runner thread bonds the binder to the bandage fabric on both sides. Depending on the strength of the bandage fabric, pressing pressures of, for example, about 3 to more than 300 bar can be applied.

Such two-sided ladder structures can, if desired, also be produced using a pair of fluted rolls of metal or plastic surface. This can be done by passing the bandage fabric perpendicularly between the pair of rolls and applying the pulverulent binder to both sides by metering it onto the rolls or into the roll nip. In this manner a plaster bandage having a two-sided ladder structure can be produced continuously and rapidly. Advantageously, the adjustment of the roll nip is continuously controlled via the pressing pressure of the roll. The rolls must run synchronously, i.e. the ridge areas of the fluted rolls and the gaps between these ridges face each other in a ridge-to-ridge-arrangement.

The inter-layer bonding of bandages coated with plaster on both sides is particularly good.

It is in general advantageous to provide the machines and tools used for applying the binder with a non-adhesive coating, for example by means of polyolefine, silicone, perfluoropolyethylene surface coatings or by using release sheet or by good polishing.

The compaction process which follows the coating process and is essential to the invention leads, if appropriate in combination with one or more sheetlike materials placed on the coating, to improved dry handling of the stiffening materials, i.e. during mechanical handling, for example winding, of the stiffening material which has not yet hydraulically set, virtually no more losses by trickling out take place. In addition, when the wound stiffening material is dipped into water, virtually no more loss by dripping off takes place. This is also the case if the hydraulic binder is arranged in the form of stripes which are parallel to the winding axis or in other patterns.

It is also possible to place more than one layer of fabric under the coating and/or to cover the binder powder before the compaction process with more than one layer of sheetlike material. The individual layers of the sheetlike material can be identical or different.

Surprisingly, compaction, for example by pressing, easily results in elimination of the free-flowability of the pulverulent hydraulic binder containing, if desired, non-reactive, preferably reactive binders, and can also attach it to relatively coarse-meshed bandage fabric, such as has previously usually been used for medical plaster bandages. The coating mixture thus attached surprisingly remains attached on the sheetlike material or between a plurality of layers of sheetlike material and does not trickle off even if the bandage is moved, for example when it is rolled up and handled.

The sheetlike materials usually used are bandage fabrics made of cotton of the bandage gauze type. They can have, for example, 25 to 35 large and 25 to 35 small meshes per $cm^2$, a ladder-like rectangular habit and weft and warp threads running in pairs at a distance of 0.5 to 1.5 and 1.5 to 2.5 mm. Other fabric and textile types are of course also possible as sheetlike materials. At coating weights of the pulverulent binder of, for example, 200 to 800 $g/m^2$, compaction is preferably carried out continuously with one passage through one or more pair(s) of rolls, whose axes are preferably arranged parallel and advantageously horizontally on top of each other or next to each other. In the case of rolls made, for example, of unprofiled, polished steel or stainless steel, nip clearances of, for example, 0.02 to 0.3 mm, preferably 0.05 to 0.1 mm, can then be selected. However, these nip clearances can change if the rolls operate, for example, with a nip which can be varied by means of a spring or is pressure-controlled, in the case of profiled rolls (for example fluted rolls or pattern rolls), or in the case of rolls having an elastically flexible plastic coating, for example made of polycarbonate or rubber. It is preferred to operate with a pair of rolls and without friction.

Fluted rolls are understood to mean those pairs of rolls in which one or both rolls, preferably only one roll, has or have a cogwheel-like cross-section perpendicular to the axis. The grooves, or flutes, on the surface may, for example, extend parallel to the axis and be V-shaped. Compaction then takes place in the form of a stripey pattern. The portion of the binder lying between the compaction stripes is then still pulverulent and can be sucked off, poured off or shaken off and reused for coating. During winding of a stiffening material compacted using fluted rolls, the stripes of the adhesive coating are parallel to the winding axis, as a result of which the material can be wound and unwound with particular ease without the coating coming off.

In this embodiment of the invention, the compaction stripes can have, for example, a width of 1 to 20 mm, preferably 2 to 6 mm, and the interstices between the compaction stripes can have, for example, a width of 0.5 to 10 mm, preferably 1 to 5 mm. In special cases, these widths can also be below these values or exceed them.

Instead of the compaction pattern in the form of stripes parallel to the axis, which is described here in more detail, it is also possible to use other compaction patterns, for example diagonal stripes, wave-like stripes or sequences of points of stripey or different arrangements. Compaction points of this type can have, for example, diameters of 1 to 20 mm, preferably 2 to 5 mm and have the form of, for example, circles, squares, rectangles or stars. Here too, the dimensions and figures selected can differ in special cases.

Compactions in the form of stripes or other patterns can be carried out virtually in all cases between rolls, for example not only by using suitable fluted rolls but also by using two smooth rolls and passing, in addition to the sheetlike material coated with pulverulent binder, flat plastic or metal parts, for example in a rope-ladder arrangement, through the rolls. In this case, compaction substantially takes place at the location of these plastic or metal parts. For example, in this manner it is possible to obtain a striped pattern if a ribbon made, for example, of plastic (for example of conventional thermoplastics, such as polyamide, polycarbonate, polyurethane, polyester or PVC) or of metal (for example of steel, aluminium or brass) in the form of a rope ladder is passed through the rolls at the same time. Such a ribbon in the form of a rope ladder can be passed through the rolls on top of and/or under, preferably under, the coated sheetlike material.

The use of polished (stainless) steel rolls is preferred. However, in order to treat, for example, the sheetlike materials with care, rubber or plastic rolls as one or both rolls of a pair of rolls are also suitable.

The rolls are preferably operated at room temperature. Reduced or elevated temperatures are also possible. In general, a temperature of 120° C., preferably 80° C., should not be exceeded.

In a particular embodiment of the compaction process, a defined amount of as-prepared pulverulent binder or binder mixture is immediately sprinkled into or incorporated in in the gusset of single- or two-layer material forming in front of the roll nip. Shaking chutes, sprinkling units and slot nozzles are, for example, suitable for this.

The density and permeability of the material wound into rolls can be controlled by means of the winding pressure, i.e. by varying the tensile forces during the winding process. Preferably, a loose roll winding is selected, such as is also customary in conventionally produced plaster bandages and which facilitates penetration of water for setting of the hydraulic binder.

It is advantageous if the mixture of plaster and additional reactive binder to be preferably used according to the invention has no tendency to dust even in the non-set state. This improves the room air situation during bandage production to a certain extent.

In the case of wound rolls containing reactive binder, this binder gradually sets. This setting process can also take place in the final package. The compaction process according to the invention in combination with such a setting of reactive binders substantially prevents the hydraulic binder incorporated in the roll from trickling out.

Following the compaction process according to the invention in combination with setting of a preferably reactive binder, the hydraulic binder is present in the form of bound, compacted, fine particles in a compact, opaque to whitish coating. Surprisingly, this structure does not impair setting of the hydraulic binder with water but allows the water to penetrate therein very quickly and uniformly upon immersion of the roll, for example, 1 to 60 seconds, preferably 2 to 10 seconds. In general, only a small excess of water is taken up by the roll. Furthermore, even in the case of longer immersion times, only little hydraulic binder is removed from the roll together with the excess water. In this manner, compared with conventional production of plaster bandages, a significant improvement in cleanliness during handling of such bandages impregnated with water is achieved. On the other hand, the bound structure impairs only slightly or not at all the spreading or modelling properties of the stiffening materials produced according to the invention.

When producing the plaster bandages in the manner according to the invention, the bandages can be cut, wound and packaged by the conventional methods of plaster bandage production. They can be cut, for example, by exposure to flames or lasers, by means of a sand or water jet, by means of ultrasound knives, blades, saws or severing discs. Other applications of stiffening materials produced according to the invention can also take place in a manner known per se.

Stiffening materials obtainable according to the invention can be used, for example, in the medical orthopaedic sector, for the production of connecting elements, impressions, masks, plugs and moulded articles, in agriculture and in horticulture, for the reinforcement of plastic parts or as protective sheathing against mechanical and/or thermal influences, for insulation, for fire protection purposes, for sealing purposes, in connection technology and for the reinforcement and stiffening of construction elements. Stiffening materials produced according to the invention, in particular plaster bandages, can be activated in the usual manner by dipping them into water for a short period in sheetlike form or wound onto suitable, for example perforated, cores. The dipping time can be, for example, 1 to 30 seconds at a temperature from 0° to 80° C., preferably 15° to 30° C.

The process according to the invention has the advantage that it is free of dust but "dry", i.e. that no solvent is required. Nor is any polluted waste air produced, which could only be purified in complicated and costly manner. This represents a great simplification compared with the prior art.

EXAMPLES

The process according to the invention is illustrated below by means of examples. Parts and percentages are by weight, unless stated otherwise.

In the examples, the following materials were used:

Strips made of cotton fabric, 10 cm wide and 300 cm long or continuous, such as usually used for the production of plaster bandages (7 weft threads, 10 warp threads per $cm^2$, mesh size $1 \times 1$ and $1 \times 2$ mm, the weight per meter of the fabric strip was 2.56 g).

Plaster powder mixture, such as is usually used as so-called hemihydrate analogous to stucco for the manufacture of plaster bandages by conventional processes.

Polyol A, a technical grade adduct of 80 mol of propylene oxide and 20 mol of ethylene oxide with sorbitol having an OH number of 175.

Polyol B, a technical grade adduct of equal parts of ethylene oxide and propylene oxide with glycerol having an OH number of 250.

Polyol C, a technical grade adduct of 60% of ethylene oxide and 40% of propylene oxide with sorbitol having an OH number of 8.

Isocyanate A, a technical grade biuretisation product of hexamethylene diisocyanate having an isocyanate content of 21%.

Isocyanate B, a technical grade polynuclear polyisocyanate from phosgenation of aniline/formaldehyde condensation products having an isocyanate content of 31%.

Isocyanate C, an oxadiazinetrione diisocyanate obtainable by reaction of 2 mol of hexamethylene diisocyanate with one mol of $CO_2$ and having an NCO content of 23%.

In a high-speed paddle mixer (Lödige mixer), the following binder mixtures were prepared at room temperature from the plaster and the polyols and polyisocyanates, all mixtures being free-flowing or sprinklable:

Mixture 1

200 parts of plaster powder were initially introduced, and a mixture of 9.3 parts of polyol A and 3.5 parts of polyisocyanate A was added.

Mixture 2

150 parts of plaster powder were initially introduced, and first 6.9 parts of polyisocyanate A and then 10 parts of polyol A were added.

Mixture 3

150 parts of plaster powder were initially introduced, and a mixture of 10 parts of polyol A and 4.6 parts of polyisocyanate B was added.

Mixture 4

150 parts of plaster powder were initially introduced, and first 10 parts of polyol B and then 4.6 parts of polyisocyanate B were added.

Mixture 5

100 parts of plaster powder were initially introduced, and 6 parts of a mixture of 100 parts of polyol C and 1.2 parts of polyisocyanate B were added.

Mixture 6

172 parts of plaster powder were initially introduced, and first 7.58 parts of polyol A and then 1.44 parts of isocyanate C were added in a paddle mixer with vigorous mixing.

EXAMPLE 1

A)

The bandage fabric, 3 m in length, was placed on a stripe-like base of smoothed paper which had been sprayed with a silicone-based release agent and was passed under a sprinkler in such a manner that, in separate batches, in each case 1 $m^2$ of the cotton fabric was coated with in each case 500 g of freshly prepared mixtures 1 to 6.

The sprinkled layer was in each case pressed in using a roller provided with a non-adhesive surface. The be sprinkled bandage fabric was then passed through the nip adjusted to a nip width of 0.07 mm of a pair of rolls consisting of polished stainless steel rolls. This compacted the coating on the fabric to give a solid opaque layer with a shiny surface, which firmly adhered to the bandage fabric. The bandage was then loosely wound into a roll (overall diameter 6 cm) on a polyolefine mandrel which had the form of a perforated tube having a diameter of 1 cm. Although the compacted layer broke in the course of the winding process at approximately regular intervals perpendicular to the longitudinal axis, it nevertheless adhered to the bandage fabric.

B)

Experiment A) was repeated, except that a second fabric of the same type was placed on the be sprinkled bandage fabric in front of the pair of rolls, lightly pressed down and the sandwich thus formed then passed through the pair of rolls. Again, a shiny, opaque, firmly adhering material layer was formed, which could be wound without bursting off.

C)

Experiment B) was repeated, except that now plaster powder was used without adding a reactive binder. After compaction in the pair of rolls, again a shiny but less opaque material sandwich which did not trickle off was obtained and wound up.

D)

Not according to the invention: Experiment B) was repeated, except that the loose sandwich composite obtained after applying the second bandage fabric and light pressing down was wound directly without passage through the pair of rolls.

The plaster loss during dry handling of the bandage material produced according to experiments A) to D) was tested as follows:

The rolls were stored in the wound state at 25° C. for 10 days, in order to allow the setting reaction of the reactive binder (if present), to proceed. 1 m of the roll weighing about 160 g and containing 3 m of bandage material was then unrolled on a flat wire screen and cut off. The piece of bandage, 1 m in length, was then rotated on the screen by hand around the long axis, so that the top side faced downwards. This procedure was repeated twice, so that ultimately the original top side faced downwards. The piece of bandage was then wound by hand on the screen onto the originally used perforated mandrel of 1 cm in diameter and removed from the screen. Finally, the plaster which had trickled through the screen during this procedure was weighed. The smaller the amount of plaster trickled through, the lower the plaster losses upon handling of the bandage containing not yet set plaster.

This test was carried out three times in each case, and the weights found of trickled-off plaster material were determined as an average value in g/m.

The following values were found:

| Bandage from experiment | A | B | C | D (not according to the invention) |
|---|---|---|---|---|
| Binder mixture | | | | |
| 1 | 4.5 | 0.9 | — | 21 |
| 2 | 7.0 | 2.1 | — | 26 |
| 3 | 4.9 | 1.3 | — | 22 |
| 4 | 4.7 | 1.3 | — | 23 |
| 5 | 5.1 | 2.0 | — | 24 |
| 6 | 4.0 | 0.9 | — | 21 |
| only plaster powder (without reactive binder) | — | — | 3.4 | — |

The results obtained show good dry handling of the bandages produced by means of the compaction according to the invention, even when no reactive binder for the plaster material is used. The results also show the effect of improvement achieved by using two fabric layers.

Analogous results were obtained by using a fabric of similar type made of high-modulus polyester yarn instead of the cotton fabric.

EXAMPLE 2

Bandages produced according to Example 1A), 1B) and 1D) using binder mixture 1 and bandages produced according to Example 1 C) were subjected to the following experiments:

After leaving the roll nip, the cotton fabric provided with the binder layer was cut to a length of 3 m, wound onto a tubular (1 cm in diameter) perforated mandrel and then sealed in polyethylene-laminated aluminium foil in a packaging unit, such as is done during plaster bandage production using the conventional method if it is desired to provide the roll before application with special protection.

For application, the rolls were removed from the package after 2 weeks. Owing to the complete setting of the reactive binder (if present) which in the meantime had taken place after the compaction process, the rolls containing the bandages from Examples 1A), 1B) and 1D) could be handled without any substantial trickling out of the plaster. All rolls were dipped perpendicularly into water at 18° C. for 4 seconds (type D for 15 seconds) and flexed slightly by hand. Only the roll containing the bandage from Example 1C) lost an appreciable amount of plaster (12 g) during this treatment. A stainless steel cylinder, 8 cm in diameter, was then wrapped therewith and smoothed. After 5 minutes, the plaster cast thus produced had stiffened. Hardening behaviour and applicability of the bandages from Examples 1 A), 1 B) and 1 D) containing the binder mixture 1 corresponded approximately to those of a 10 cm plaster bandage equipped with 600 g of plaster material per m² and produced in the usual manner, except that the impregnating water and the aqueous phase pushed out during milling had much less the character of aqueous plaster and more that of slightly cloudy water, thus making possible a much cleaner operation than with customary plaster bandages.

After hardening, the plaster cast thus produced and wound into rolls was slipped off the cylinder and dried at 21° C. to constant weight.

The 10 cm wide roll was then placed sideways on a balance and pressed down from the top in the middle with a 6 cm² round stamp. The achievable maximum load-bearing capacity of the roll was then read off the balance as the maximum value. It is a measure of the strength of the roll.

These experiments were repeated five times using different rolls of the same type, and the measured results gave an average value of the strength from the five individual measurements, as shown in the table below:

| Hardened plaster cast after slipping-off containing a bandage from Example | Strength (kg) |
|---|---|
| 1 A) containing binder mixture 1 | 63 |
| 1 A) containing binder mixture 6 | 64 |
| 1 B) containing binder mixture 1 | 68 |
| 1 C) without reactive binder | 62 |
| 1 D) containing binder mixture 1 | 65 |

For a plaster bandage produced in the usual manner (without compaction and without reactive binder), a strength of 59 kg was found in an analogous manner.

This means that the strengths of the rolls obtained by the process according to the invention are, after setting, of the same order of magnitude as or better than in the case of conventional plaster bandages. The results also show that the sandwich structure leads to an improvement in strength, which in combination with the solvent-free and technically simple production process, the good dry handling and the low plaster losses upon impregnation constitutes a significant technical and ecological advance.

EXAMPLE 3

The procedure of Example 1A) using the binder mixture 1 and the procedure of Example 1C) was repeated, except that one roll of the pair of rolls was replaced by a roll fluted parallel to the axis having web widths of 3.4 mm, interstice widths of 1.5 mm and interstice depths of 2.5 mm. The nip width of the rolls between the fluted roll and the smooth roll was adjusted to 0.085 mm. The bandage fabric was uniformly sprinkled with 800 g/m² of binder.

The now intermittent compaction process attached the binder to the bandage fabric in stripe form perpendicular to the fabric length on the fabric. During transport of the bandage following the passage through the pair of rolls to a unit for cutting to length and winding, the amount of binder not compacted by the flutes of the roll was made to trickle through the holes in the fabric by gentle shaking and returned to the coating process. The compaction regions adhered through the fabric webs and were incorporated in the roll.

This coating arrangement gives particularly good wind-ability and dry handling. When the roll was dipped perpendicularly into water, dipping times of about 2 seconds were sufficient for complete moistening of the roll. Application behaviour and final strengths were analogous to those of the products from Examples 1A) and 1C).

Analogous results were obtained by sprinkling a mixture of equal parts by weight of Portland cement and binder mixture onto the fabric.

EXAMPLE 4

A 3 m roll stored for 2 weeks and obtained according to 1B) using binder mixture 1 was unrolled while dry and folded to a stack of 20 cm in length. This unrolling and folding to a stack resulted in small plaster losses by trickling off of less than 4.5 g. The stack was then dipped into water for 3 seconds, while maintaining its geometry, allowed to drip dry by holding it upright, during which almost no plaster paste dripped off, and then incorporated as a longuette in a hand stiffening bandage wound onto a model (finger/wrist region). In this case, hardening took place analogously to conventional plaster cast materials within 3 to 6 minutes.

EXAMPLE 5

On the adhesive side of a textile adhesive tape, 4 m in length and 12 cm in width, extruded polycarbonate stripes, 12 cm in length, 3 mm in width and 2 mm in thickness, were placed parallel at a spacing of 2 mm and pressed firm, leading to a ribbon of the tank-track or rope-ladder structure type. This ribbon was placed under the bandage fabric and then sprinkled with 600 g/m$^2$ of a plaster/binder mixture, resulting in uniform sprinkling over the area of the fabric. The plaster/binder mixture had been obtained by thorough mixing of 200 parts of hemihydrate (plaster powder) first with 7.65 parts of polyol C.

The be sprinkled fabric was then passed together with the "tank-track" underneath through a pair of smooth stainless steel rolls arranged on top of each other (nip width 2.07 mm). Via a deflecting roller, at which the portion of the sprinkled-on powder not compacted by the polycarbonate elements of the "tank-track", trickled off and was returned to the sprinkler, the bandage material which now had a type of rope-ladder structure was wound loosely into a roll having a diameter of 6 cm. The roll being present on a perforated, tubular plastic mandrel of 1 cm in diameter was then packed into a tight-sealing polyethylene can.

After 7 days, the roll was removed and completely wetted by immersion in water (19° C., immersion time 3 seconds, perpendicular immersion direction). The water running off was only slightly cloudy and did not have the character of aqueous plaster. The plaster bandage was very cleanly unrollable and convertible into a test plaster cast as described in Example 2. Upon testing the dry handling according to Example 1, the plaster loss was 1.5 g/m and the strength of the test plaster cast obtained according to Example 2 was 64 kg, which is within the standard range. Owing to the rope-ladder structure, the bandage of this type could be unrolled similarly to the bandage obtained according to Example 4 but without breaking the plaster coating and thus with an even smaller plaster loss to give longuettes and processed.

EXAMPLE 6

Example 5 was repeated, except that a plaster/binder mixture was used for sprinkling which had been obtained by thorough mixing of 170 parts of plaster powder with 7.58 parts of polyol A and 1.45 parts of isocyanate C. The properties in practical application were similar to those in Example 5.

What is claimed is:

1. A process for the production of stiffening materials containing a hydraulic binder, in which a hydraulic binder in powder form is applied to a flexible substrate in an amount of 200 to 800 g/m$^2$, the hydraulic binder is compacted in contact with the flexible substrate by guiding it through a roll nip having a width of 0.02 to 0.3 mm or by compacting it by means of a stamp or a press until it loses its flowability, and the flexible substrate thus provided with compacted hydraulic binder is wound into rolls.

2. The process of claim 1, in which compaction of the hydraulic binder is carried out on one layer of flexible substrate.

3. The process of claim 1, in which compaction of the hydraulic binder is carried out between two or more layers of flexible substrate.

4. The process of claim 1, in which the hydraulic binder is arranged on the flexible substrate in the form of multiple discrete stripes on one side.

5. The process of claim 1, in which the hydraulic binder is arranged on the flexible substrate in the form of multiple discrete stripes on both sides.

6. The process of claim 1, in which a reactive binder is mixed with the hydraulic binder prior to compaction.

7. A process for the production of plaster bandages usable in medicine in which a plaster-based hydraulic binder is mixed with a reactive binder to produce a binder mixture, the binder mixture is applied to a flexible substrate in an amount of 200 to 800 g/m$^2$, said binder mixture is compacted until it loses its flowability by guiding it through a roll nip having a width of 0.02 to 0.3 mm or by compacting it by means of a stamp or a press, the product thus provided with a compacted binder layer is wound into rolls and wherein the reactive binder is set in a setting reaction before, during and/or after winding.

8. A process for the production of plaster bandages usable in medicine in which a plaster-based hydraulic binder is mixed with a reactive binder to produce a binder mixture, said mixture is applied to a flexible substrate in an amount of 200 to 800 g/m$^2$ to produce a coating, the coating thus obtained is covered with a further flexible substrate, said covered coating is compacted until it loses its flowability by guiding it through a roll nip having a width of 0.02 to 0.3 mm or by compacting it by means of a stamp or a press, the product thus provided with a compacted binder layer is wound into rolls and the reactive binder is set in a setting reaction before, during and/or after winding.

9. The process of claim 1, in which the hydraulic binder used is selected from the group consisting of partially hydrated gypsum, α-gypsum, β-gypsum, anhydride, Portland cement, high-alumina cement, aluminosilicate cement, Sorell cement, zinc oxide cement, puzzolan cement and mixtures thereof.

10. The process of claim 1, in which a reactive binder, selected from the group consisting of silicates, epoxides, polyepoxides, epoxy-curing agents, cyanoacrylates, acrylates, vinyl esters, allyl ethers, silanes, siloxanes, silicones, alkyd resins, cyanate resins, phenolic resins, formaldehyde resins, methylol compounds, and methylol ethers and isocyanates which react to form polyurethanes, polyureas, polycarbodiimides or polyisocyanurates, is applied to the flexible substrate in addition to the hydraulic binder.

11. The process of claim 1, wherein the hydraulic binder is applied in a mixture of said hydraulic binder and a reactive binder, and the mixture is up to 50% by weight of reactive binder, relative to the hydraulic binder.

12. The process of claim 1, in which compaction is carried out by means of a passage through one or more pair(s) of rolls.

13. The process of claim 1, wherein the hydraulic binder is compacted using said roll nip and wherein at least one roll of said roll nip is a profiled roll having flutes or patterns, and wherein the compaction takes place in the form of stripes or patterns.

14. The process of claim 1, wherein a polyisocyanate and a polyol are applied to the flexible substrate in addition to the hydraulic binder.

* * * * *